United States Patent [19]

Hopf

[11] Patent Number: 5,446,169

[45] Date of Patent: Aug. 29, 1995

[54] PROCESS FOR THE PREPARATION OF 3(3-CARBOXY-PROPYL)-5-METHOXYINDOLE-2-CARBOXYLIC ACID

[75] Inventor: Martin Hopf, Gross-Zimmern, Germany

[73] Assignee: Merck Patent Gesellschaft Mit Beschrankter Haftung, Darmstadt, Germany

[21] Appl. No.: 275,476

[22] Filed: Jul. 15, 1994

[30] Foreign Application Priority Data

Jul. 17, 1993 [DE] Germany ............... 43 24 043.7

[51] Int. Cl.⁶ ........................................... C07D 209/42
[52] U.S. Cl. ................................... 548/502; 548/492
[58] Field of Search ............................................ 548/495

[56] References Cited

PUBLICATIONS

Hausberg et al., "Indole-alkyl-piperidines, a New Class of Dopamine Agonists", Acta Pharmaceutica Suecica, Suppl. 1983:2, 20–23 Apr. 1982.

Clack et al., "Electrophilic Substitution in Indoles, etc . . . ", J. Chem. Soc., Perkin Trans. II 1982, pp. 909–916.

*Primary Examiner*—David B. Springer
*Attorney, Agent, or Firm*—Millen, White, Zelano & Branigan

[57] ABSTRACT

The invention relates to a new process for the preparation of 3-(3-carboxypropyl)-5-methoxyindole-2-carboxylic acid (I), characterized in that 6-carboethoxy-6-p-methoxyphenylhydrazonohexanoic acid (II) is cyclized using a carboxylic acid which contains 1–3 carbon atoms, the resulting mixture comprising I, the two I monoethyl esters and I diethyl ester is treated with a strong inorganic base, and the resulting salt is converted into the free acid I by treatment with a strong acid.

4 Claims, No Drawings

PROCESS FOR THE PREPARATION OF 3(3-CARBOXY-PROPYL)-5-METHOXYINDOLE-2-CARBOXYLIC ACID

The invention relates to a new process for the preparation of 3-(3-carboxypropyl)-5-methoxyindole-2-carboxylic acid (I).

This compound has been prepared up to now by reacting 6-carboethoxy-6-p-methoxyphenylhydrazonohexanoic acid (II) with sulphuric acid/ethanol to give I diethyl ester (simultaneous esterification), isolating the latter and then subjecting it to hydrolysis with ethanolic sodium hydroxide solution. However, the overall yield in this process (54%) was not satisfactory.

The object of the invention was to discover an improved process for the preparation of I.

It has been found that the cyclization of II can also be carried out using a carboxylic acid which contains 1–3 carbon atoms. Admittedly, the product is a mixture of the dicarboxylic acid I with its monoethyl and diethyl esters. However, this mixture can be treated directly with a strong inorganic base and subsequently acidified, with I being obtained in a good yield.

The invention relates to a process for the preparation of 3-(3-carboxypropyl)-5-methoxyindole-2-carboxylic acid (I), characterized in that 6-carboethoxy-6-p-methoxyphenylhydrazonohexanoic acid (II) is cyclized using a carboxylic acid which contains 1–3 carbon atoms, the resulting mixture comprising I, the two I monoethyl esters and I diethyl ester is treated with a strong inorganic base, and the resulting salt is converted into the free acid I by treatment with a strong acid.

The acid I can be used as an intermediate in the production of Roxindol, see U.S. Pat. Nos. 4,914,114 and 4,251,538.

The cyclization of II using the carboxylic acid is expediently carried out at temperatures of between 20 and 120°, preferably at boiling temperature. The reaction times are between about 1 and 200 hours, preferably between 10 and 30 hours. It is advantageous to use from approximately 0.5 to 10, preferably from 1 to 2, parts by weight of carboxylic acid, based on II. The carboxylic acid is preferably used in anhydrous form. A low water content (up to about 10%) reduces the yield by a few per cent, but is otherwise not harmful higher water contents lead to poorer yields. The preferred carboxylic acid is acetic acid, but formic acid or propionic acid is also highly suitable.

Advantageously the reaction mixture is subsequently concentrated by evaporation and the mixture obtained is treated with a strong inorganic base, preferably with an alkali metal hydroxide, in particular KOH but also, for example, NaOH, or with an alkaline earth metal hydroxide, for example Ca(OH)$_2$, in an inert solvent or solvent mixture, for example an alcohol such as methanol, ethanol or isopropanol or water or an alcohol/water mixture, at temperatures of between about 20 and 120°, preferably between 60° and 100°.

The mixture is finally acidified, advantageously using a strong acid, for example a mineral acid such as hydrochloric acid or sulphuric acid, after which the free acid I precipitates. It is advantageous first to neutralize the product, to clarify the solution using active charcoal and subsequently to add further mineral acid to pH<2.

6-Carboethoxy-6-p-methoxyphenylhydrazonohexanoic acid can be prepared by reaction of diazotized p-methoxyaniline with ethyl 1-oxycyclohexane-2-carboxylate according to the well-known Japp-Klingemann-type Fischer indole synthesis (cf. *Proceedings of the Symposium on Dopamine Receptor Agonists*, Acta Pharmaceutica Suecica (Suppl.) 1983, 2, 213–217;J. Chem. Soc. Perkin Trans. II 1982, 909–916).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application(s) German P 43 24 043.7, filed Jul. 17, 1993, are hereby incorporated by reference.

EXAMPLE

A mixture of 66 g of II and 100 g of acetic acid is boiled for 21 hours. The acetic acid is distilled off, the residue is dissolved in 120 ml of ethanol, 74 g of 85% KOH and 75 ml of water are added, and the mixture is stirred at 80° C. for 2 hours. The mixture is then concentrated by evaporation. The residue is dissolved in 200 ml of water, hydrochloric acid is added to pH 7.5, the solution is treated with active charcoal and filtered, and hydrochloric acid is added to the filtrate to pH<2. The precipitated free acid I is filtered off, washed with water and dried. Yield 45.4 g; m.p. 192°–194° (from acetic acid).

The preceding example can be repeated with similar success by substituting the generically or specifically described reactants and/or operating conditions of this invention for those used in the preceding example.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 3-(3-carboxypropyl)-5-methoxyindole-2-carboxylic acid (I), wherein 6-carboethoxy-6-p-methoxyphenylhydrazonohexanoic acid (II) is cyclized using a carboxylic acid which contains 1–3 carbon atoms to provide a mixture comprising I, the two I monoethyl esters and I diethyl ester.

2. A process as in claim 1, wherein the mixture comprising I, the two I monoethyl esters and I diethyl ester is further treated with an inorganic base to form a salt.

3. A process as in claim 2, wherein the salt is converted into the free acid I by treatment with an acid.

4. A process for the preparation of 3-(3-carboxypropyl)-5-methoxyindole-2-carboxylic acid (I), wherein 6-carboethoxy-6-p-methoxyphenylhydrazonohexanoic acid (II) is cyclized using a carboxylic acid which contains 1–3 carbon atoms, the resulting mixture comprising I, the two I monoethyl esters and I diethyl ester is treated with a strong inorganic base, and the resulting salt is converted into the free acid I by treatment with a strong acid.

* * * * *